United States Patent
Blum et al.

(10) Patent No.: US 8,393,588 B2
(45) Date of Patent: Mar. 12, 2013

(54) ADAPTOR FOR FIXING A MEDICAL APPARATUS

(75) Inventors: Stefanie Blum, Munich (DE); Steffi Blechinger, Munich (DE); Holger Rossner, Feldkirchen (DE); Richard Wohlgemuth, Bad Tolz (DE)

(73) Assignee: Brainlab AG, Feldkirchen (DE)

( * ) Notice: Subject to any disclaimer, the term of this patent is extended or adjusted under 35 U.S.C. 154(b) by 611 days.

(21) Appl. No.: 12/501,545

(22) Filed: Jul. 13, 2009

(65) Prior Publication Data

US 2010/0012798 A1 Jan. 21, 2010

Related U.S. Application Data

(60) Provisional application No. 61/100,284, filed on Sep. 26, 2008.

(51) Int. Cl.
*F16M 11/00* (2006.01)

(52) U.S. Cl. .............. 248/228.6; 248/230.6; 248/231.71; 248/176.1

(58) Field of Classification Search ............... 248/228.6, 248/230.6, 231.71, 689, 222.52, 223.41, 248/224.51, 224.61, 415, 176.1, 187.1
See application file for complete search history.

(56) References Cited

U.S. PATENT DOCUMENTS

| | | | |
|---|---|---|---|
| 3,221,743 A | 12/1965 | Thompson et al. | |
| 5,553,198 A | 9/1996 | Wang et al. | |
| 5,657,429 A | 8/1997 | Wang et al. | |
| 7,546,993 B1 * | 6/2009 | Walker | 248/218.4 |
| 7,719,437 B2 * | 5/2010 | Bertram, III | 340/815.73 |
| 7,891,621 B1 * | 2/2011 | Secora et al. | 248/292.12 |
| 2006/0151676 A1 * | 7/2006 | Harvey | 248/229.15 |
| 2008/0116340 A1 * | 5/2008 | Greene | 248/229.15 |
| 2009/0078840 A1 * | 3/2009 | Wolvin | 248/229.15 |
| 2009/0146033 A1 * | 6/2009 | Chiang | 248/284.1 |

FOREIGN PATENT DOCUMENTS

| | | |
|---|---|---|
| EP | 1 190 680 | 3/2002 |
| WO | 02/065933 | 8/2002 |
| WO | 02/085187 | 10/2002 |

* cited by examiner

*Primary Examiner* — Terrell McKinnon
*Assistant Examiner* — Steven Marsh
(74) *Attorney, Agent, or Firm* — Renner, Otto, Boisselle & Sklar, LLP

(57) ABSTRACT

An adaptor for fixing a medical apparatus to one or two support structures, wherein the adaptor is constructed in three parts from a bearing part and two support parts, wherein the bearing part can be connected to the medical apparatus, the first support part can be connected to a first support structure and the second support part can be connected to a second support structure, and the adaptor can assume at least three states, wherein: in the first state, the bearing part is connected free of clearance to the first support part only; in the second state, the bearing part is connected free of clearance to the second support part only; and in the third state, the bearing part is connected free of clearance to the first support part and the second support part.

12 Claims, 5 Drawing Sheets

ADAPTOR FOR FIXING A MEDICAL APPARATUS

RELATED APPLICATION DATA

This application claims the priority of U.S. Provisional Application No. 61/100,284, filed on Sep. 26, 2008, which is hereby incorporated in its entirety by reference.

FIELD OF THE INVENTION

The present invention relates to an adaptor for fixing a medical apparatus to one or two support structures.

BACKGROUND OF THE INVENTION

In medical applications, apparatuses are often used which are heavy or which have to be guided extremely precisely. It is therefore necessary to provide mountings for such apparatuses. U.S. Pat. No. 5,657,429 and U.S. Pat. No. 5,553,198, for example, each disclose a robot system in which a robot arm can be fastened by means of an adaptor on a cart or to an operating table. The robot arm is fixedly connected to the adaptor and connected via a mechanism either to the operating table or to the cart.

SUMMARY OF THE INVENTION

It is the object of the present invention to provide an adaptor for fixing a medical apparatus to a support structure, which is simpler in its construction and can be used more flexibly.

This object is solved by an adaptor for fixing a medical apparatus to one or two support structures, wherein the adaptor is constructed in three parts from a bearing part and two support parts, wherein the bearing part can be connected to the medical apparatus, the first support part can be connected to a first support structure and the second support part can be connected to a second support structure, and the adaptor can assume at least three states, wherein: in the first state, the bearing part is connected free of clearance to the first support part only; in the second state, the bearing part is connected free of clearance to the second support part only; and in the third state, the bearing part is connected free of clearance to the first support part and the second support part. The object is also solved by a medical system comprising such an adaptor. Advantageous embodiments may be gathered from the dependent patent claims.

In accordance with the invention, an adaptor for fixing a medical apparatus to one or two support structures is constructed in three parts from a bearing part and two support parts, wherein the bearing part can be connected to the medical apparatus, the first support part can be connected to a first support structure and the second support part can be connected to a second support structure. The first support structure is for example an operating table and/or a rail fastened to an operating table. The second support part is for example a stand which can be horizontally moved and vertically adjusted in height, and in which the wheels can optionally be retracted, such that the foot of the stand rests firmly on the ground. The medical apparatus is for example a robot arm.

In accordance with the invention, the adaptor can assume at least three connecting states, wherein: in the first state, the bearing part is connected free of clearance to the first support part only; in the second state, the bearing part is connected free of clearance to the second support part only; and in the third state, the bearing part is connected free of clearance to the first support part and the second support part. The third state offers the advantage that the first support structure, for example an operating table, can be additionally borne by the second support structure via the adaptor and so additionally stabilized, in particular when the medical apparatus exhibits a large weight and thus exerts a torque on the first support structure. In one specific embodiment of a connection which is free of clearance, the parts which are connected to each other are fixed relative to each other, such that no rotational or translational relative movement between the parts is possible.

In a preferred embodiment of the invention, the bearing part and the first support part can be connected to each other free of clearance in exactly one position. This relative position is also referred to as an end position between the two parts. This means that the relative position between the bearing part and the first support part when the two parts are connected is known exactly. The position of the medical apparatus relative to the first support structure is therefore also known.

In order to be reciprocally connected to each other, the bearing part and the first support part are advantageously designed such that they can be shifted, in particular vertically. To this end, the bearing part comprises for example a shifting part, in particular a plate, which is designed to be attached to an element of the first support part, such that it can be shifted, i.e. for example inserted into pocket-like rails on the first support part or attached to a rod of the support part, such that it can be shifted. The shifting part of the bearing part is inserted into the rails on the first support part in order to establish a connection between the two parts. The rails preferably comprise an end stopper for the shifting part, if the shifting part and therefore the bearing part is situated in its end position in which the bearing part and the first support part are fixedly connected to each other free of clearance, wherein the first support part is preferably arranged on the first support structure such that the pocket-like rails run in the vertical direction. The force of gravity acting on the bearing part then presses the shifting part towards the base of the pocket formed by the rails.

The pocket-like rails on the first support part also preferably comprise at least one oblique abutment surface at their end. Since a small clearance should be provided between the pocket-like rails and the shifting part, in order to insert the shifting part into the rails with as little friction as possible, the oblique abutment surface ensures, in the end position, a defined abutment of the shifting part in the pocket-like rails and therefore on the first support part. The surface is for example beveled in the shape of a wedge. If, as preferred, the rails are vertically aligned, the force of gravity generates a clamping force between the rails and the shifting part which results in a connection which is free of clearance.

In one embodiment of the invention, a fixing device for fixing the bearing part relative to the first support part is arranged on the first support part. The shifting part is for example fixedly clamped in the pocket-like rails by the fixing device. Fixing using the fixing device is performed in addition to or as an alternative to fixing using the force of gravity.

The adaptor preferably comprises a centering aid for simplifying the connection between the bearing part and the first support part. The centering aid consists for example of one or more oblique surfaces which centre the bearing part as it approaches the first support part and/or as the plate on the bearing part is inserted into the pocket-like rails on the first support part.

The adaptor preferably comprises a lock for securing the bearing part relative to the first support part. The lock is for example a shearing clamp, an eccentric lever, a sprung eccentric lever or a chamfered bolt. When closed, the lock prevents the bearing part and the first support part from separating.

In one preferred embodiment of the invention, the bearing part and the second support part can be connected to each other free of clearance in a number of relative positions. This means that it is possible, via the adaptor, to fix the two support structures free of clearance in various relative positions of the support structures. Thus, for example, a second support part which is attached on a stand can be connected to the bearing part free of clearance at a number of heights of the stand, for example when the stand is adjusted in height or has been lowered onto the ground. This can for example be enabled by the second support part comprising a cylindrical base part which can be inserted into a sleeve-like region of the bearing part. The second support part and the bearing part can then be connected to each other free of clearance in a number of axially shifted positions of the cylindrical base part relative to the bearing part. The sleeve-like region and the cylindrical base part thus form a shifting sleeve which can be clamped, wherein the term "axially" refers to the centre axis of the cylindrical base part, which is identical to the centre axis of the sleeve-like region of the bearing part. This axis preferably points in the direction of gravity, i.e. it lies in the vertical.

The sleeve-like region of the bearing part consists for example of two half-shells which are connected to each other by means of a hinge and can be locked using a locking mechanism. The locking mechanism is for example based on a clamping lever or an eccentric lever. Locking the sleeve-like region results in a cylindrical pressing brace between the bearing part and the cylindrical base part of the second support part. The relative position of the support part and the bearing part is thus held free of clearance due to friction.

Another way of connecting the bearing part and second support part free of clearance is a clamping mechanism in which a region of one of the two parts can be spread and presses onto an interior or exterior region of the other part in each case.

The adaptor preferably comprises a centering aid for simplifying the connection between the bearing part and the second support part. This is for example a chamfer on the exterior side of the cylindrical base part of the second support part which can be inserted into the sleeve-like region of the bearing part. Alternatively or additionally, the sleeve-like region of the bearing part comprises a funnel-shaped chamfer on the side from which the cylindrical base part of the second support part can be inserted into the sleeve-like region of the bearing part.

The adaptor is preferably embodied such that the connection between the bearing part and the second support part can only be separated when a connection exists between the bearing part and the first support part. This is for example achieved by means of a pin which prevents a relative movement between the bearing part and the second support part. The block provided by the pin is for example released by moving the pin out of engagement using a lever mechanism, as soon as the bearing part has reached its end position relative to the first support part. The lever mechanism is for example arranged on the bearing part and is operated by the first support part. The lever mechanism is preferably biased using a spring, such that the pin is automatically moved into engagement when the lever mechanism is not operated.

Preferably, at least one of the three parts of the adaptor, in particular the first support part, can be sterilized. This preferably relates to all the components which the sterilizable part consists of. The three parts and/or their components are for example made of aluminum or an aluminum alloy such as $AlMg_{4.5}Mn$.

The invention also relates to a medical system comprising a medical apparatus, a first support structure, a second support structure and an adaptor such as has been described above. The first support part of the adaptor is connected to the first support structure, the second support part of the adaptor is connected to the second support structure, and the bearing part of the adaptor is connected to the medical apparatus. The medical apparatus can for example be a robot arm, a microscope, an ultrasound apparatus, an x-ray apparatus, an operating lamp or a 3D camera for image-assisted navigation. The position of the two support structures and the medical apparatus relative to each other is determined by the position of the parts of the adaptor relative to each other. The first support structure is for example an operating table; the second support structure is for example a stand. The operating table for example comprises a rail to which the first support part is fastened. This can be achieved by a screw connection which is either designed rigidly or comprises a shutter mechanism. An eccentric clamping lever can alternatively be used.

The medical system preferably comprises at least one sensor for detecting the state of the adaptor. The state of the adaptor is composed of various sub-states. Possible sub-states are for example a contact between the bearing part and the first support part, an end position of the bearing part in relation to the first support part, an advancing movement of the bearing part relative to the first support part, a fixed connection between the bearing part and the first support part, a fixed connection between the bearing part and the second support part, a contact between the bearing part and the second support part or an advancing movement of the second support part relative to the bearing part.

Preferably, one or more of the aforesaid sub-states are detected, wherein for example one sensor is provided for each sub-state to be detected. On the basis of the output data of the sensor or sensors, the medical apparatus can for example only be used when the bearing part is fixedly connected to at least one of the support parts. The medical apparatus is otherwise prevented from being used. Another possibility is that the second support structure can only be moved—for example, a stand can only be lowered (i.e. adjusted in the vertical)— when a fixed connection exists between the bearing part and the first support part. A sensor is for example an optical, mechanical or electromechanical switch. A sensor for detecting a contact between two parts detects for example an electrical contact between the two parts, for example by measuring the potential at one part while a test potential is applied to the other part.

In one embodiment of the invention, a marker device is arranged on at least one of the parts of the adaptor. A marker device is a device whose spatial position and/or alignment can be automatically determined, for example by means of a detection device such as a 3D camera. The detection device is for example part of a navigation system, which is for example used in image-assisted navigation or IGS (image-guided surgery). A marker device consists for example of three spheres in a known spatial arrangement. From the position of a marker device, it is possible to deduce the position of the corresponding part of the adaptor and therefore the position of the medical apparatus or of a support structure, for example absolutely or in relation to a(nother) support structure or an anatomical structure which can be treated with the aid of the medical apparatus. This information can for example be used for navigating the medical apparatus connected to the adaptor or another medical apparatus.

BRIEF DESCRIPTION OF THE DRAWINGS

The present invention shall be illustrated in more detail on the basis of an example embodiment, wherein.

DETAILED DESCRIPTION

Figure 1A:
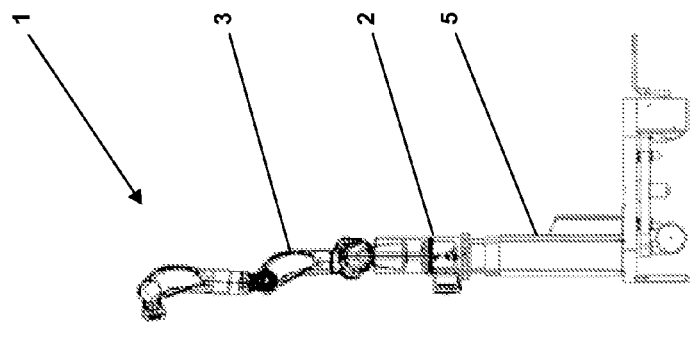
FIGS. 1a-1c show a medical system in three states.
Figure 1B:
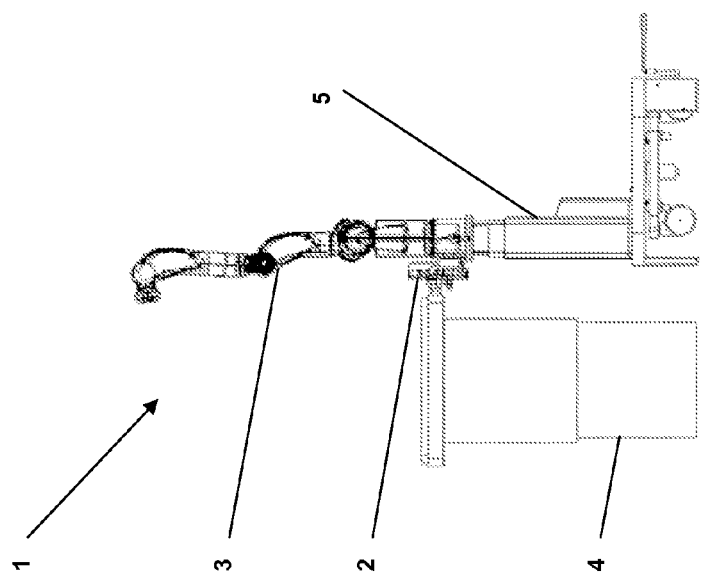
Figure 1C:
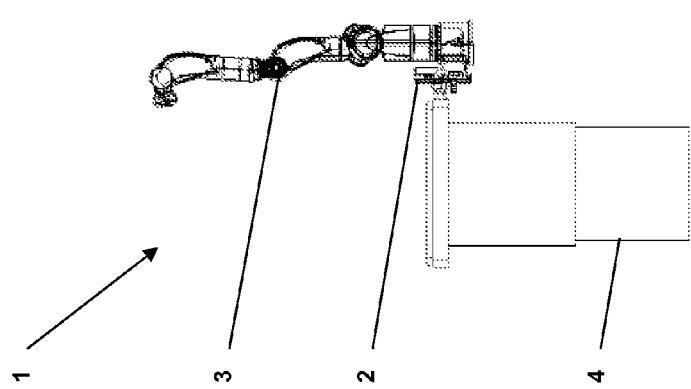

FIGS. 1a to 1c show a medical system 1 comprising: a medical apparatus in the form of a robot arm 3; an operating table 4; a stand 5; and an adaptor 2. The operating table 4, and the stand 5—which can be horizontally moved, vertically adjusted in height and lowered onto its feet—constitute support structures for the robot arm 3. By means of the adaptor 2, the robot arm 3 can be fastened to the operating table 4 only (see FIG. 1a), to both the operating table 4 and the stand 5 (see FIG. 1b), or to the stand 5 only (see FIG. 1c).

Figure 2:
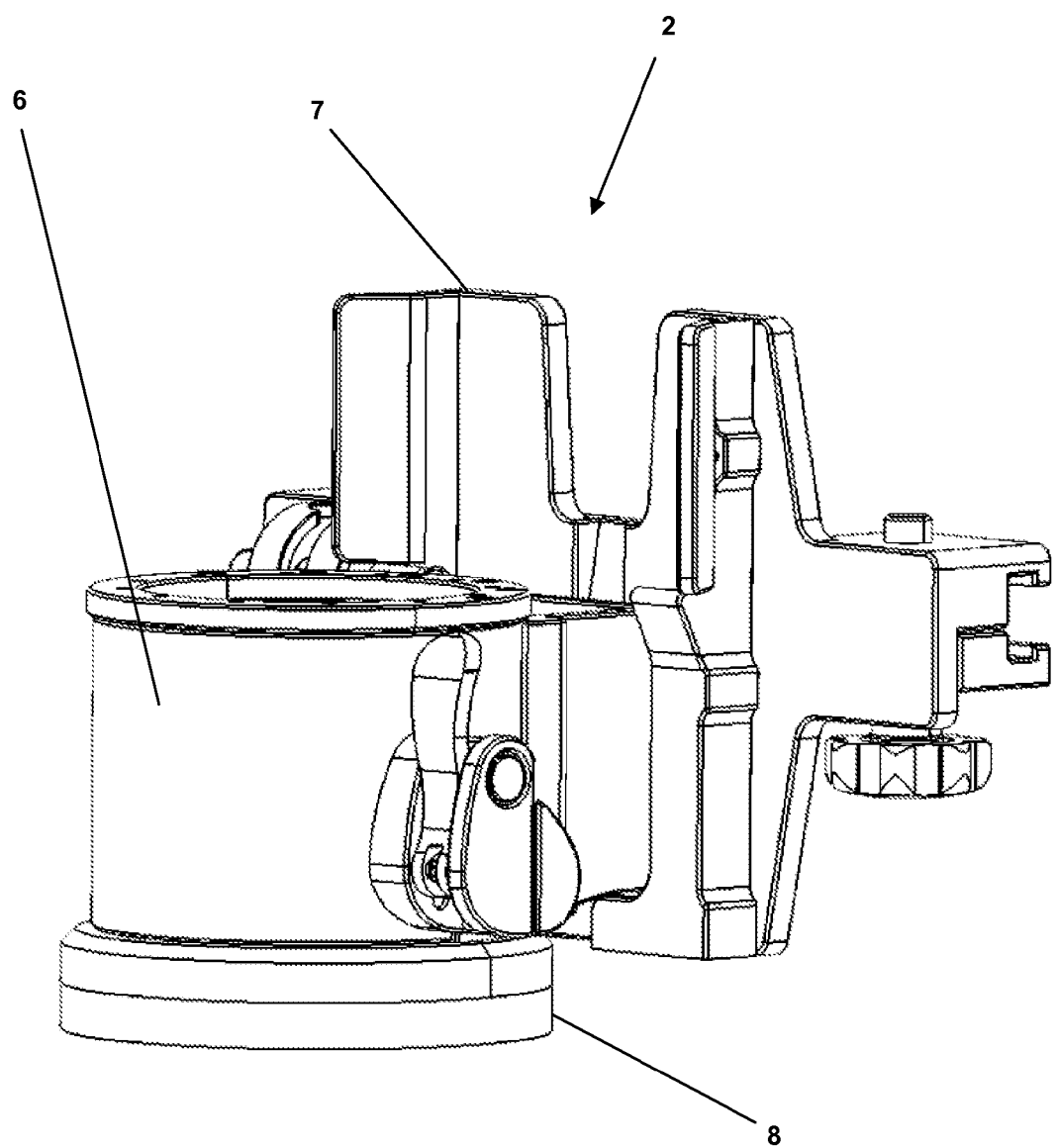
FIG. 2 shows a three-part adaptor.
Figure 6:
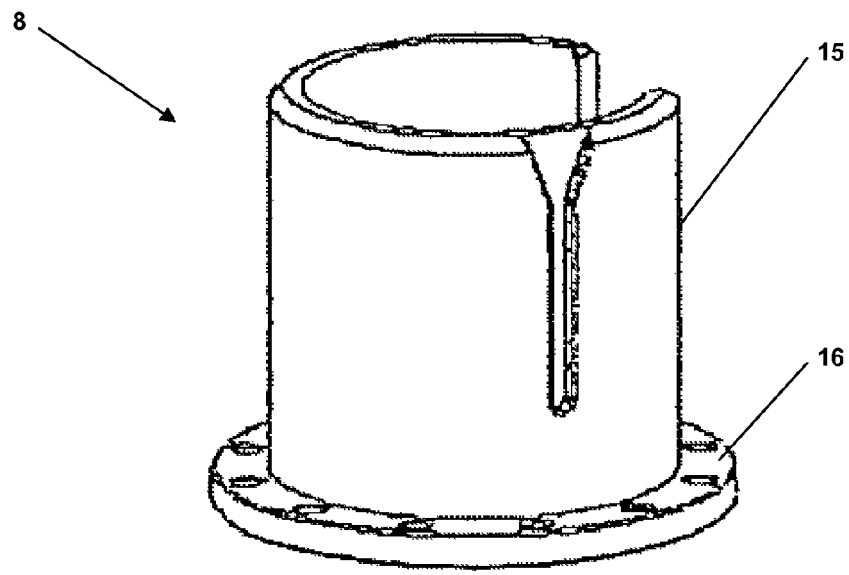
FIG. 6 shows the second support part of the adaptor from FIG. 2.

The adaptor 2 is shown in more detail in FIG. 2. It comprises a bearing part 6 (see also FIG. 3) which is fixedly connected to the robot arm 3. A first support part 7 of the adaptor 2 (see FIGS. 5a to 5c) is fastened to the operating table 4; a second support part 8 (see FIG. 6) is fixedly fastened to the stand 5.

FIG. 1a shows a first state of the medical system 1 and therefore of the adaptor 2, in which the robot arm 3 is fastened to the operating table 4 only. The operating table 4 and a patient situated on it are thus optimally accessible for a surgeon. In this state, the bearing part 6 of the adaptor 2 is connected free of clearance to the first support part 7 only.

In the state shown in FIG. 1b, the stand 5 has been moved under the bearing part 6 and deployed, and a connection between the bearing part 6 and the second support part 8 has been established. Accordingly, the bearing part 6 of the adaptor 2 is respectively connected free of clearance to both the first support part 7 and the second support part 8. The weight of the robot arm 3 is thus borne by both the operating table 4 and the stand 5, such that the static and dynamic forces caused by the inherent weight and movement of the robot arm 3 are borne by two support structures, and a movement of the operating table 4 is thus reduced or avoided. The stand 5 can for example be lowered, such that it rests on a base part or foot instead of on wheels and thus exhibits an even greater stability.

If the robot arm 3 is to be removed from the operating table 4, then the connection between the bearing part 6 of the adaptor 2 and the first support part 7 is released. If the stand is then deployed, or the lowering onto the base part is reversed, the robot arm 3 is then borne by the stand 5 only, as shown in FIG. 1c.

Figure 3:
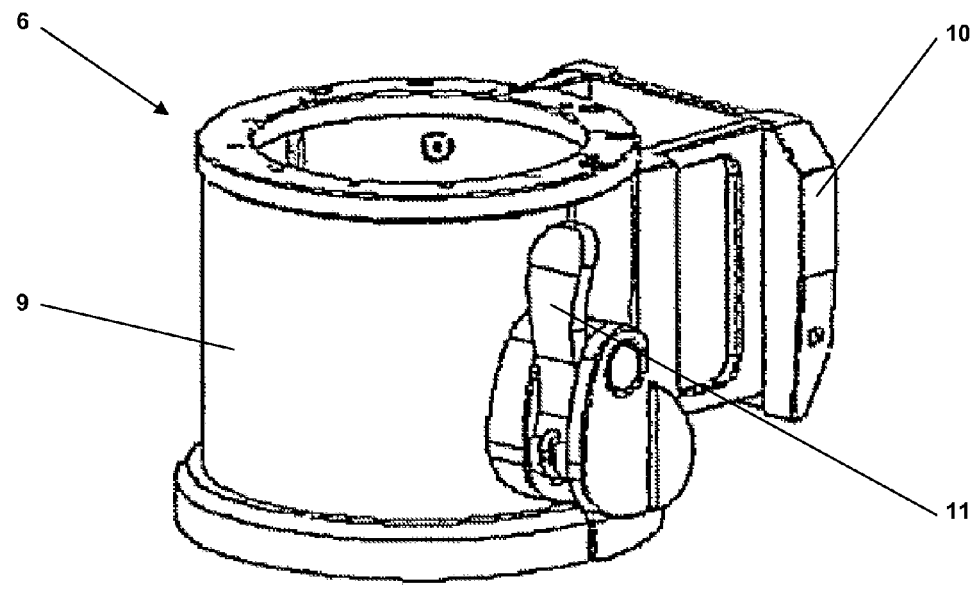
FIG. 3 shows the bearing part of the adaptor from FIG. 2.

FIG. 3 shows a three-dimensional view of the bearing part 6. The bearing part 6 substantially consists of a sleeve-like region 9 and a plate 10. The sleeve-like region 9 serves to fix the bearing part 6 to the second support part 8 free of clearance; the plate 10 serves to connect the bearing part 6 to the first support part 7 free of clearance.

Figure 4:
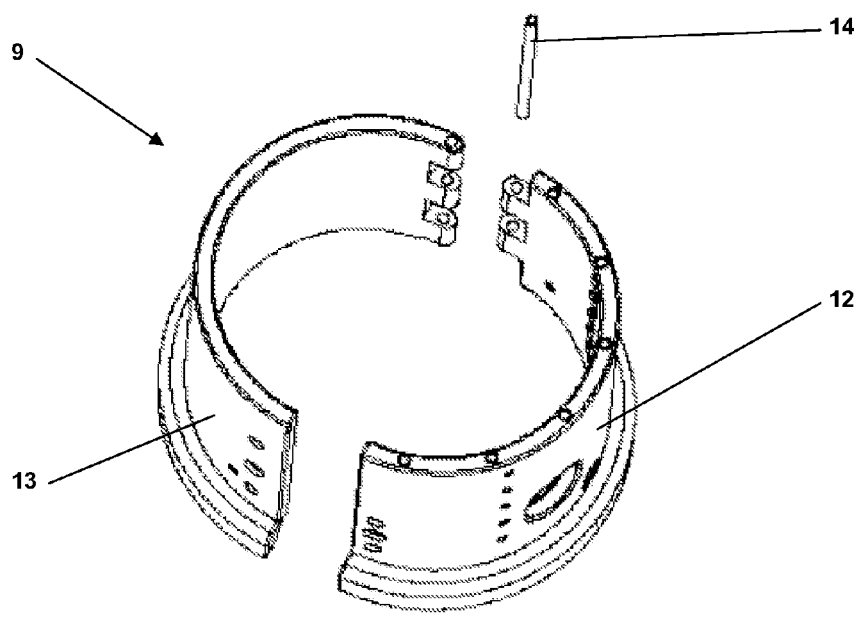
FIG. 4 shows an exploded representation of the sleeve-shaped part of the bearing part.

As shown in FIG. 4, the sleeve-like region 9 substantially consists of two half-shells 12 and 13 which are connected on one of their connecting lines, by means of a pin 14, in the manner of a hinge. The two half-shells 12 and 13 are thus able to form a cylindrical interior space. The eccentric lever 11, shown in FIG. 3, is provided at the other connecting line between the two half-shells 12 and 13, in order to close the two half-shells 12 and 13, i.e. move them towards each other.

When the two half-shells 12 and 13 are closed, a clamping force is exerted on a cylindrical base part 15 of the second support part 8 (see FIG. 6) between the half-shells 12 and 13, such that a fixation which is free of clearance exists between the bearing part 6 and the second support part 8. The second support part 8 also comprises a flange 16, by means of which it is screwed on the stand 5.

The exterior edge of the base part 15, which can be inserted into the sleeve-like region 9 of the bearing part 6, is beveled and thus forms a centering aid which simplifies inserting the second support part 8 into the sleeve-like region 9 of the bearing part 6.

Due to the cylindrical pressing fit of the second support part 8 in the bearing part 6, it is possible to fix the two parts to each other free of clearance in various relative positions. In this way, height compensation can for example be provided.

Figure 5A:
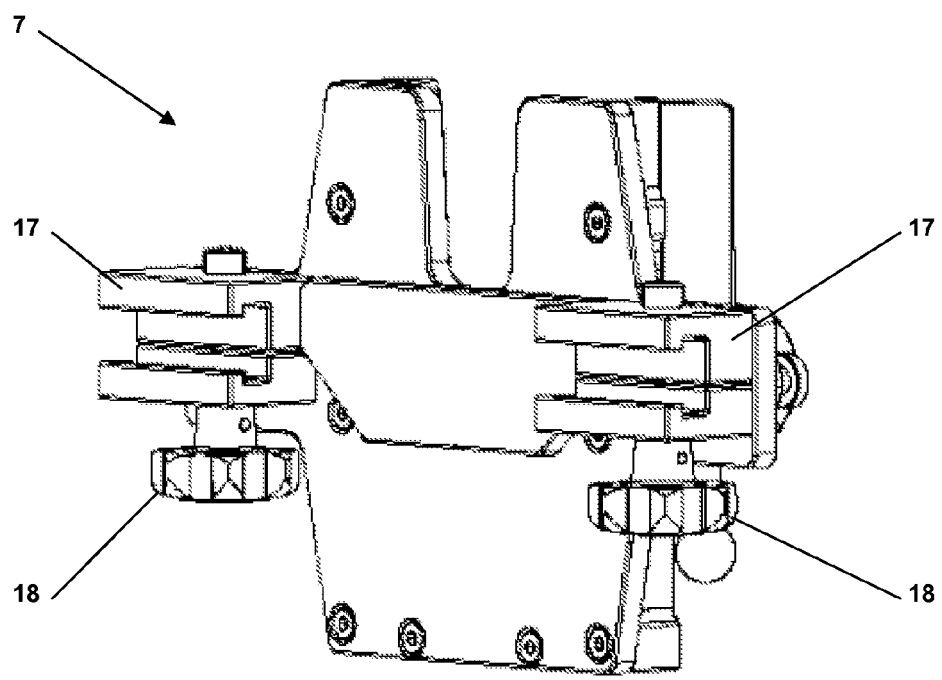
FIGS. 5a-5c shows three views of the first support part of the adaptor from FIG. 2.
Figure 5B:
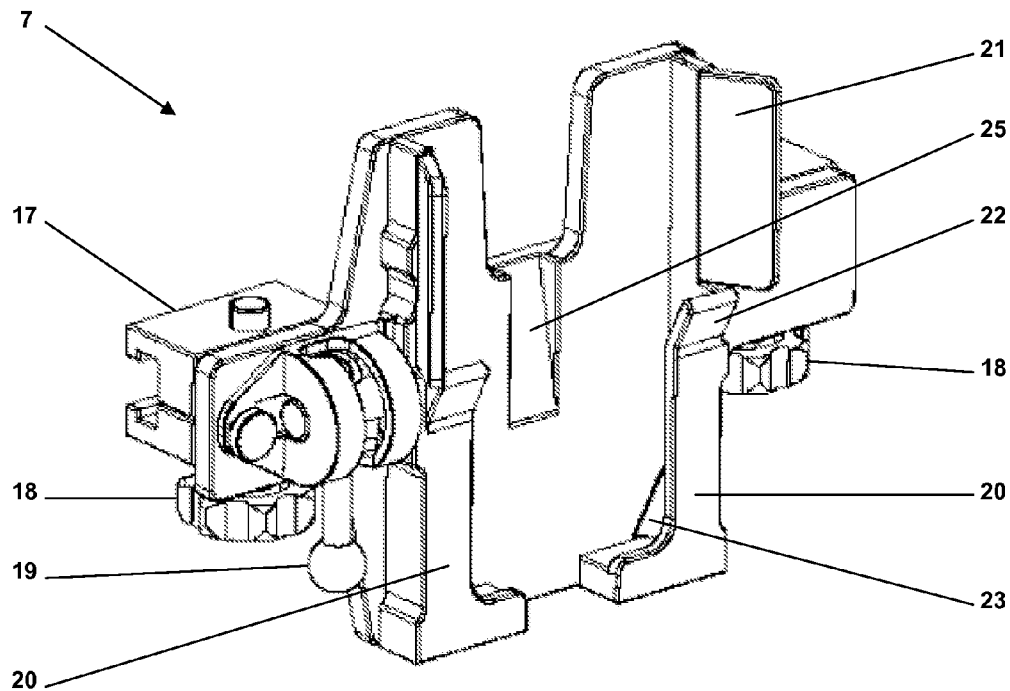
Figure 5C:
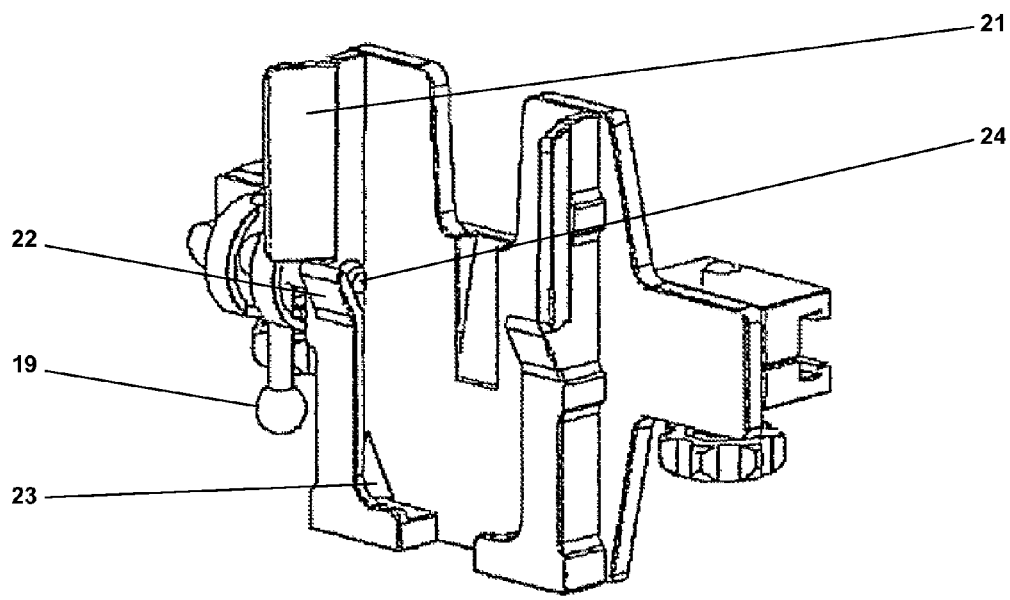

FIGS. 5a to 5c show three different three-dimensional views of the first support part 7. In the rear view in FIG. 5a, two C-shaped clamps 17 can be seen, by means of which the first support part 7 is fastened to a rail arranged on the operating table 4. Using knurled screws 18, a clamping force is applied which fixes the first support part 7 securely to the rail and therefore to the operating table 4.

FIGS. 5b and 5c show the front side of the first support part 7 from different viewing directions. Two pocket-like rails 20, into which the plate 10 of the bearing part 6 can be inserted, are formed on the front side of a base plate of the first support part 7. In order to simplify inserting the plate 10 into the rails 20, a centering aid comprising two oblique guiding surfaces 21 and two other oblique guiding surfaces 22 is provided. As the bearing part 6 approaches the first support part 7, the plate 10 is guided by the guiding surfaces 21 which extend in the shape of a funnel, thus horizontally centering the plate 10 perpendicular to the direction of approach. As the plate 10 is lowered into the pocket formed from the rails 20, the two oblique guiding surfaces 22 ensure that it is horizontally centered in the aforesaid direction of approach.

In order to ensure that the plate 10 sits in the pocket free of clearance, two oblique guiding surfaces 23 are provided at the base of the pocket, between the base plate, the base of the pocket and the sides of the rails 20. The plate 10 slides off on these guiding surfaces 23 until it sits in the rails 20 free of clearance due to the force of gravity. Production tolerances in the plate 10 or rails 20 can be compensated for using the oblique guiding surfaces 23.

The connection which is free of clearance between the first support part 7 and the bearing part 6 is ensured by the inherent weight of the bearing part 6 and in particular of the robot arm 3 connected to it. The weight presses the plate 10 onto the base of the pocket formed by the rails 20, until the plate 10 slips over the guiding surfaces 23 into its end position. The plate 10 is thus fixed relative to the first support part 7, both in the horizontal direction and in the direction of gravity. Due to the inherent weight of the bearing part 6 and the robot arm 3, it is not possible for the plate 10 to be lifted out of the pocket-like rails 20 without a deliberate external application of force.

When the plate 10 is situated in its end position at the base of the pocket formed by the rails 20, the plate 10 and therefore the bearing part 6 is additionally secured by moving the lever 19. Moving the lever 19 moves a bolt 24 into an arresting position in which it prevents the plate 10 from being removed from the rails 20. Optionally, the bolt 24 not only fulfils a securing function but also helps to fix the bearing part 6 and first support part 7 free of clearance, by preventing any freedom of movement of the plate 10 upwards. Alternatively, the bearing part 6 and first support part 7 are fixed free of clearance by the bolt 24 only.

The rails 20 form a guiding device between the first support part 7 and the bearing part 6; the sleeve-like region 9 forms a guiding device between the second support part 8 and the bearing part 6. The guiding devices, the plate 10 on the bearing part 6 and the cylindrical base part 15 on the second support part 8 are embodied and arranged such that the advancing direction of the plate 10 in the rails 20 and the advancing direction of the base part 15 in the sleeve-like region 9 are parallel to each other. These advancing directions are preferably orientated vertically, i.e. in the direction of gravity.

The medical system 1 comprises four optional sensors. The first sensor monitors whether a contact exists between the bearing part 6 and the first support part 7. The second sensor monitors whether the lever 19 is situated in a position in which the bolt 24 prevents the plate 10 from slipping out of the pocket-like rails 20. The third sensor monitors whether a contact exists between the bearing part 6 and the second support part 8. The fourth sensor monitors whether the lever 11 is situated in a position in which the sleeve-like region 9 exerts a clamping force on the base part 15 of the second support part 8.

Control electronics (not shown) prevent the robot arm 3 from being operated when it is not fastened to at least one support structure, i.e. to the operating table 4 or the stand 5. The robot arm 3 is fastened to the operating table 4 when the first sensor detects a contact between the bearing part 6 and the first support part 7 and the second sensor detects a closed bolt 24. A fixed connection between the robot arm 3 and the stand 5 exists when the third sensor detects a contact between the bearing part 6 and the second support part 8 and the fourth sensor detects the closed state of the lever 11. The output data of the four sensors can also be used to allow the height of the stand 5 to be adjusted only when the bearing part 6 is fixed relative to the first support part 7.

A securing device (which cannot be seen in the figures) prevents a relative movement of the cylindrical base part 15 of the second support part 8 in the sleeve-like region 9 of the bearing part 6 as long as the plate 10 of the bearing part 6 is not situated in its end position in the pocket, formed from the rails 20, on the first support part 7. To this end, a bolt is for example used which blocks the aforesaid relative movement in one position. This bolt is moved radially away from the centre axis of the sleeve-like region 9 using a lever mechanism, when the lever slides over the oblique surface 25 in the base plate of the first support part 7. This is the case when the plate 10 of the bearing part 6 is pushed into the pocket, formed from the rails 20, on the first support part 7.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. An adaptor for fixing a medical apparatus to one or two support structures, wherein the adaptor is constructed in three parts from a bearing part and two support parts,
wherein the bearing part can be connected to the medical apparatus, a first support part can be connected to a first support structure and a second support part can be connected to a second support structure, and
the adaptor can assume at least three states, wherein: in the first state, the bearing part is connected free of clearance to the first support part only; in the second state, the bearing part is connected free of clearance to the second support part only; and in the third state, the bearing part is connected free of clearance to the first support part and the second support part, the adaptor further comprising:
a shifting part on the bearing part which is designed to be inserted into pocket-like rails on the first support part, and
at least one oblique abutment surface at the end of the pocket-like rails on the first support part.

2. The adaptor according to claim 1, wherein the bearing part and the first support part can be connected to each other free of clearance in exactly one position.

3. The adaptor according to claim 1, comprising a centering aid for simplifying the connection between the bearing part and the first support part.

4. The adaptor according to claim 1, comprising a lock for securing the bearing part relative to the first support part.

5. The adaptor according to claim 1, wherein the bearing part and the second support part can be connected to each other free of clearance in a number of relative positions.

6. The adaptor according to claim 1, wherein the second support part comprises a cylindrical base part which can be inserted into a sleeve-like region of the bearing part.

7. The adaptor according to claim 1, comprising a centering aid for simplifying the connection between the bearing part and the second support part.

8. A medical system, comprising a medical apparatus, a first support structure, a second support structure and an adaptor according to claim 1.

9. An adaptor for fixing a medical apparatus to one or two support structures, wherein the adaptor is constructed in three parts from a bearing part and two support parts,
   wherein the bearing part can be connected to the medical apparatus, the first support part can be connected to a first support structure and a second support part can be connected to a second support structure, and
   the adaptor can assume at least three states, wherein: in the first state, the bearing part is connected free of clearance to the first support part only; in the second state, the bearing part is connected free of clearance to the second support part only; and in the third state, the bearing part is connected free of clearance to the first support part and the second support part,
   wherein the second support part comprises a cylindrical base part which can be inserted into a sleeve-like region of the bearing part, and
   wherein the sleeve-like region of the bearing part consists of two half-shells which are connected to each other by means of a hinge and can be locked using a locking mechanism.

10. An adaptor for fixing a medical apparatus to one or two support structures, wherein the adaptor is constructed in three parts from a bearing part and two support parts,
    wherein the bearing part can be connected to the medical apparatus, a first support part can be connected to a first support structure and a second support part can be connected to a second support structure, and
    the adaptor can assume at least three states, wherein: in the first state, the bearing part is connected free of clearance to the first support part only; in the second state, the bearing part is connected free of clearance to the second support part only; and in the third state, the bearing part is connected free of clearance to the first support part and the second support part, and
    wherein the connection between the bearing part and the second support part can only be separated when a connection exists between the bearing part and the first support part.

11. A medical system comprising a medical apparatus, a first support structure, a second support structure and an adaptor for fixing a medical apparatus to one or two support structures, wherein the adaptor is constructed in three parts from a bearing part and two support parts,
    wherein the bearing part can be connected to the medical apparatus, a first support part can be connected to a first support structure and a second support part can be connected to a second support structure, and
    the adaptor can assume at least three states, wherein: in the first state, the bearing part is connected free of clearance to the first support part only; in the second state, the bearing part is connected free of clearance to the second support part only; and in the third state, the bearing part is connected free of clearance to the first support part and the second support part, and
    further comprising at least one sensor for detecting a state of the adaptor.

12. The medical system according to claim 8, comprising a marker device on at least one of the parts of the adaptor.

* * * * *

UNITED STATES PATENT AND TRADEMARK OFFICE
CERTIFICATE OF CORRECTION

| | | |
|---|---|---|
| PATENT NO. | : 8,393,588 B2 | Page 1 of 1 |
| APPLICATION NO. | : 12/501545 | |
| DATED | : March 12, 2013 | |
| INVENTOR(S) | : Stefanie Blum et al. | |

It is certified that error appears in the above-identified patent and that said Letters Patent is hereby corrected as shown below:

Title page, Item (30), Foreign Application Priority Data should be added:
-- (30)     Foreign Application Priority Data
   Jul. 16, 2008   (EP) .............................. 08160536 --

Signed and Sealed this
Twenty-first Day of May, 2013

Teresa Stanek Rea
*Acting Director of the United States Patent and Trademark Office*